US012226257B2

(12) United States Patent
Kinomoto

(10) Patent No.: US 12,226,257 B2
(45) Date of Patent: Feb. 18, 2025

(54) ULTRASONIC ENDOSCOPE

(71) Applicant: FUJIFILM Corporation, Tokyo (JP)

(72) Inventor: Noboru Kinomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 344 days.

(21) Appl. No.: 17/900,875

(22) Filed: Sep. 1, 2022

(65) Prior Publication Data
US 2022/0409174 A1 Dec. 29, 2022

Related U.S. Application Data

(63) Continuation of application No. PCT/JP2021/011308, filed on Mar. 19, 2021.

(30) Foreign Application Priority Data

Mar. 26, 2020 (JP) ................................. 2020-055658

(51) Int. Cl.
*A61B 8/00* (2006.01)
*A61B 1/00* (2006.01)
*A61B 1/06* (2006.01)

(52) U.S. Cl.
CPC .................. *A61B 8/44* (2013.01); *A61B 1/06* (2013.01); *A61B 8/4483* (2013.01); *A61B 1/00114* (2013.01)

(58) Field of Classification Search
None
See application file for complete search history.

(56) References Cited

U.S. PATENT DOCUMENTS 9,636,009 B2 * 5/2017 Ogawa ............... G02B 23/2476
10,285,573 B2 * 5/2019 Nishina .................. A61B 1/009
(Continued)

FOREIGN PATENT DOCUMENTS

JP 2013198566 10/2013
JP 2019122671 7/2019
(Continued)

OTHER PUBLICATIONS

"International Search Report (Form PCT/ISA/210) of PCT/JP2021/011308," mailed on May 18, 2021, with English translation thereof, pp. 1-5.
(Continued)

*Primary Examiner* — Ricky Chin
(74) *Attorney, Agent, or Firm* — JCIPRNET

(57) ABSTRACT

Provided is an ultrasonic endoscope with which it is possible to prevent damage to an imaging element even in a case where voltage from an external power supply is directly applied. A distal end portion main body (43) of an ultrasonic endoscope (10) is formed of a resin material, the distal end portion main body (43) includes an illumination system (53) that includes an illumination metal base (156), a first fixing member (170) that fixes the illumination metal base (156) to the distal end portion main body (43), a first insert hole (172) into which the first fixing member (170) is inserted, an observation system (55) that includes a lens barrel (160), a second fixing member (174) that fixes the lens barrel (160) to the distal end portion main body (43), a second insert hole (176) into which the second fixing member (174) is inserted, and an electrical connection member (178) that electrically connects the illumination metal base (156) and the lens barrel (160), and at least one of the illumination metal base (156), the lens barrel (160), or the electrical connection member (178) is connected to a ground.

12 Claims, 12 Drawing Sheets

(56) References Cited

U.S. PATENT DOCUMENTS

| | | | |
|---|---|---|---|
| 2013/0286786 A1* | 10/2013 | Yoshida | B06B 1/02 |
| | | | 367/140 |
| 2015/0087993 A1* | 3/2015 | Sato | A61B 8/4483 |
| | | | 310/300 |
| 2016/0331216 A1* | 11/2016 | Kaneko | A61B 1/00006 |
| 2017/0265715 A1* | 9/2017 | Nishina | A61B 1/009 |
| 2017/0303893 A1* | 10/2017 | Sato | A61B 8/445 |
| 2018/0168541 A1* | 6/2018 | Kitahara | A61B 8/5261 |
| 2019/0090847 A1* | 3/2019 | Yamamoto | A61B 8/44 |
| 2019/0133559 A1* | 5/2019 | Okada | H10N 30/875 |
| 2019/0298321 A1* | 10/2019 | Intintoli | A61B 1/07 |
| 2020/0015664 A1* | 1/2020 | Hatase | A61B 1/07 |
| 2020/0320702 A1* | 10/2020 | Kamon | A61B 1/0655 |
| 2021/0142901 A1* | 5/2021 | Usuda | G16H 30/40 |
| 2021/0338066 A1* | 11/2021 | Tsuruta | A61B 1/018 |
| 2021/0369238 A1* | 12/2021 | Uchihara | A61B 8/12 |
| 2021/0378635 A1* | 12/2021 | Kumata | A61B 8/4488 |
| 2022/0104875 A1* | 4/2022 | Gleiman | A61B 18/1492 |
| 2022/0361846 A1* | 11/2022 | Hiraoka | A61B 8/445 |
| 2022/0409174 A1* | 12/2022 | Kinomoto | A61B 1/00096 |
| 2022/0409175 A1* | 12/2022 | Kinomoto | A61B 1/00096 |

FOREIGN PATENT DOCUMENTS

| | | | | |
|---|---|---|---|---|
| JP | 2020010745 | | 1/2020 | |
| WO | 2014208218 | | 12/2014 | |
| WO | 2016203830 | | 12/2016 | |
| WO | WO-2018003322 A1 | * | 1/2018 | A61B 8/12 |
| WO | WO-2018003737 A1 | * | 1/2018 | A61B 8/12 |
| WO | WO-2019082891 A1 | * | 5/2019 | A61B 1/00114 |
| WO | WO-2019087266 A1 | * | 5/2019 | A61B 8/12 |

OTHER PUBLICATIONS

"Written Opinion of the International Searching Authority (Form PCT/ISA/237)" of PCT/JP2021/011308, mailed on May 18, 2021, with English translation thereof, pp. 1-6.

* cited by examiner

ULTRASONIC ENDOSCOPE

CROSS-REFERENCE TO RELATED APPLICATIONS

The present application is a Continuation of PCT International Application No. PCT/JP2021/0011308 filed on Mar. 19, 2021 claiming priority under 35 U.S.C § 119(a) to Japanese Patent Application No. 2020-055658 filed on Mar. 26, 2020. Each of the above applications is hereby expressly incorporated by reference, in its entirety, into the present application.

BACKGROUND OF THE INVENTION

1. Field of the Invention

The present invention relates to an ultrasonic endoscope, and particularly to an ultrasonic endoscope that includes an observation system provided at a distal end portion of an insertion portion.

2. Description of the Related Art

An ultrasonic endoscope is used in the medical field. Regarding the ultrasonic endoscope, an imaging element and an ultrasonic transducer are integrally disposed at a distal end portion of an insertion portion which is to be inserted into the body cavity of a subject.

Since the ultrasound oscillator of the ultrasonic endoscope is driven by a high voltage, the distal end portion needs to be formed of a resin material. However, in a case where the distal end portion is formed of a resin material and static electricity hits the distal end portion, the imaging element may be damaged by the static electricity transmitted thereto since the static electricity cannot be released unlike in a case where the distal end portion is formed of a metal material. Therefore, in order to solve such a problem, for example, a jump wire is disposed such that a lens barrel of an observation lens and a ground terminal provided on a substrate are electrically connected to each other.

However, in a case where only the above-described measure is taken and static electricity hits an illumination metal base, a treatment tool insertion channel, a fluid jetting nozzle, and the like, the imaging element may be damaged by the static electricity running through a space between the above-described members and the imaging element and directly hitting the imaging element. Particularly, since an observation system and an illumination system are disposed close to each other for acquisition of a bright endoscopic image, static electricity may fly from the illumination metal base to the imaging element.

A member that covers the imaging element is provided or a member that covers the illumination metal base, a forcep pipe, or the like is provided so that static electricity is prevented from flying to the imaging element from a member that is disposed at a distal end portion main body and is formed of metal. As an endoscope in which a lens barrel and an illumination metal base are connected to each other, an endoscope that includes a first through-hole into which an observation system is inserted, a second through-hole into which an illumination system is inserted, and a holding frame formed of metal is described in WO2014/208218A. In addition, described in WO2016/203830A is an endoscope in which a first objective lens frame and an illumination lens frame are integrated with each other via a continuation portion (conductive adhesive) so that the first objective lens frame and the illumination lens frame are electrically connected to each other.

SUMMARY OF THE INVENTION

As described in WO2014/208218A and WO2016/203830A, with electrical connection between a lens barrel, an illumination metal base, and the ground, static electricity hitting the illumination metal base can be prevented from being transmitted to an imaging element. However, in WO2014/208218A and WO2016/203830A, the holding frame or the continuation portion is used, which results in an increase in endoscope diameter. Furthermore, in a case where a reduction in endoscope diameter is needed, use of the holding frame or the like is restricted. In a case where the holding frame or the like is not used, a jump wire for grounding each of the lens barrel and the illumination metal base is needed and thus the number of necessary members is increased. In addition, even in a case where a contactor that extends the illumination metal base and the lens barrel is provided, the filling rate of the inside of the endoscope is increased, which may hinder insertion of internal components.

The present invention has been made in consideration of such circumstances and an object thereof is to provide an ultrasonic endoscope with which it is possible to prevent an increase in diameter of a distal end portion of the ultrasonic endoscope and to prevent damage to an imaging element even in a case where static electricity is directly applied to the distal end portion.

According to an aspect of the present invention, there is provided an ultrasonic endoscope including a distal end portion including a distal end portion main body that is provided at a distal end side of an insertion portion and is formed of a resin material and an ultrasound oscillator that is provided at the distal end portion main body. The distal end portion main body includes an illumination system that includes an illumination lens, a fiber, and a first metal member holding the illumination lens and the fiber, a first insertion hole into which the first metal member is inserted, a first fixing member that fixes the first metal member inserted into the first insertion hole to the distal end portion main body and that has conductivity, a first insert hole into which the first fixing member is inserted, an observation system that includes an observation lens, a second metal member holding the observation lens, and a substrate on which an imaging element is mounted, a second insertion hole into which the second metal member is inserted, a second fixing member that fixes the second metal member inserted into the second insertion hole to the distal end portion main body and that has conductivity, a second insert hole into which the second fixing member is inserted, and an electrical connection member that electrically connects the first fixing member and the second fixing member to each other, and at least one of the first metal member, the second metal member, or the electrical connection member is connected to a ground.

In an aspect of the present invention, the first insert hole and the second insert hole are preferably formed along a direction orthogonal to a longitudinal axis of the insertion portion, the first insert hole preferably penetrates into the first insertion hole from a side surface of the distal end portion main body, and the second insert hole preferably penetrates into the second insertion hole from the side surface of the distal end portion main body.

In an aspect of the present invention, the first fixing member and the second fixing member are preferably screws, and the electrical connection member is preferably a metal plate that is disposed on an outer circumference of the distal end portion main body and that includes a contact surface coming into contact with the screws.

In an aspect of the present invention, the first fixing member and the second fixing member are preferably conductive adhesives, and the electrical connection member is preferably a metal plate that is disposed on an outer circumference of the distal end portion main body and that includes a contact surface coming into contact with the conductive adhesives.

In an aspect of the present invention, the first fixing member and the second fixing member are preferably compression springs, and the electrical connection member is preferably a metal plate that is disposed on an outer circumference of the distal end portion main body and that includes a contact surface coming into contact with the compression springs.

In an aspect of the present invention, the first fixing member, the second fixing member, and the electrical connection member are preferably conductive adhesives, silver paste, or solder, and the first fixing member, the second fixing member, and the electrical connection member are preferably an integrally molded piece obtained by connecting the conductive adhesives, the silver paste, or the solder filling the first insert hole and the second insert hole by the conductive adhesives, the silver paste, or the solder disposed along an outer circumference of the distal end portion main body.

In an aspect of the present invention, the first fixing member, the second fixing member, and the electrical connection member are preferably conductive rubbers, and the first fixing member, the second fixing member, and the electrical connection member are preferably an integrally molded piece.

In an aspect of the present invention, the ultrasonic endoscope preferably further includes a cap that includes a pressing surface pressing and fixing the electrical connection member to the distal end portion main body.

In an aspect of the present invention, the distal end portion main body preferably includes a fluid jetting nozzle, a third fixing member that fixes the fluid jetting nozzle to the distal end portion main body and that has conductivity, and a third insert hole into which the third fixing member is inserted, and the electrical connection member preferably includes a contact surface that comes into contact with the third fixing member.

In an aspect of the present invention, the distal end portion main body preferably includes a treatment tool insertion channel, a fourth fixing member that fixes the treatment tool insertion channel to the distal end portion main body and that has conductivity, and a fourth insert hole into which the fourth fixing member is inserted, and the electrical connection member preferably includes a contact surface that comes into contact with the fourth fixing member.

In an aspect of the present invention, the connection to the ground is preferably connection between a ground terminal provided on the substrate and the second metal member.

In an aspect of the present invention, the insertion portion preferably includes a metal ring group consisting of a plurality of angle rings connected to a proximal end side of the distal end portion main body, a fifth fixing member that fixes the metal ring group to the distal end portion main body and that has conductivity and a fifth insert hole into which the fifth fixing member is inserted are preferably provided, and the connection to the ground is preferably connection between the fifth fixing member and the second metal member.

According to the aspects of the present invention, it is possible to prevent damage to an imaging element even in a case where voltage from an external power supply is directly applied to a distal end portion of an ultrasonic endoscope.

DESCRIPTION OF THE PREFERRED EMBODIMENTS

Hereinafter, preferred embodiments of an ultrasonic endoscope according to an embodiment of the present invention will be described with reference to the accompanying drawings.

Figure 1:
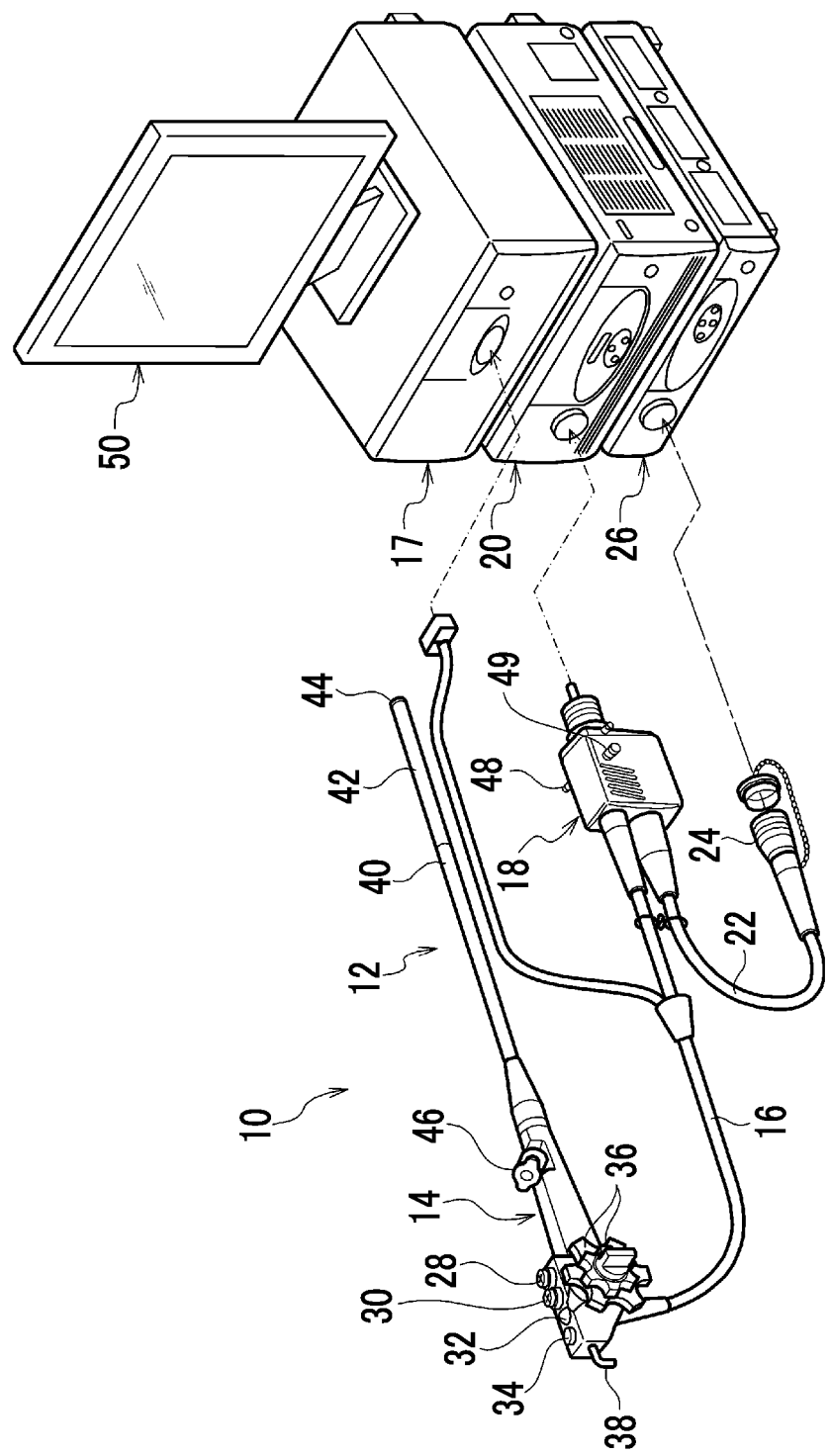
FIG. 1 is a system configuration view of an endoscope apparatus including an ultrasonic endoscope.
Figure 2:
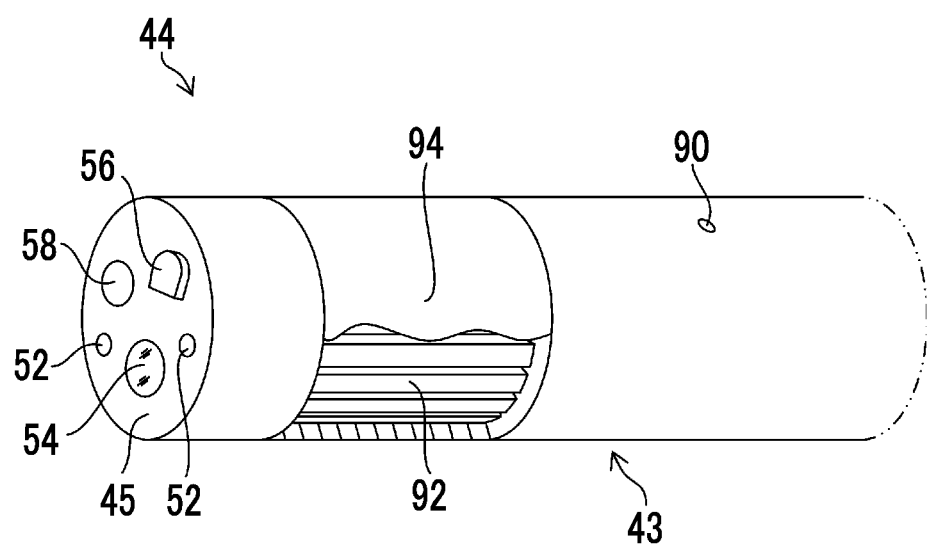
FIG. 2 is a perspective view showing a distal end portion of an insertion portion of the ultrasonic endoscope.
Figure 3:
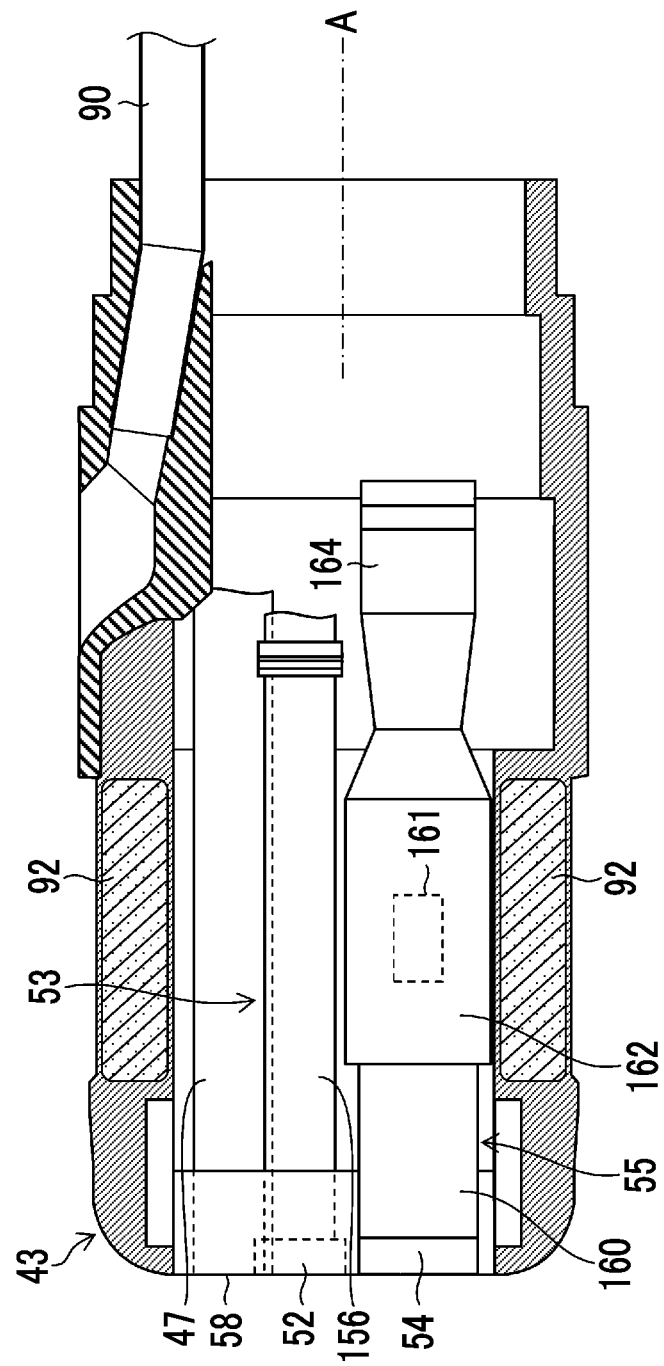
FIG. 3 is a side cross-sectional view of the distal end portion of the ultrasonic endoscope.
Figure 4:
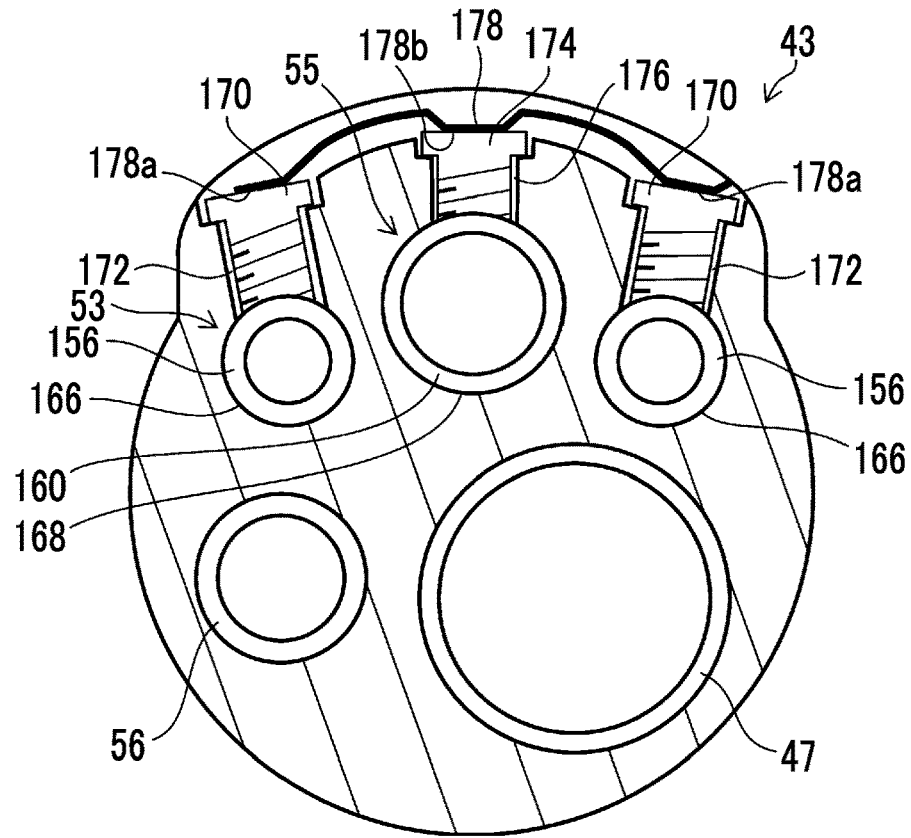
FIG. 4 is a vertical cross-sectional view of a distal end portion main body of the ultrasonic endoscope.
Figure 5:
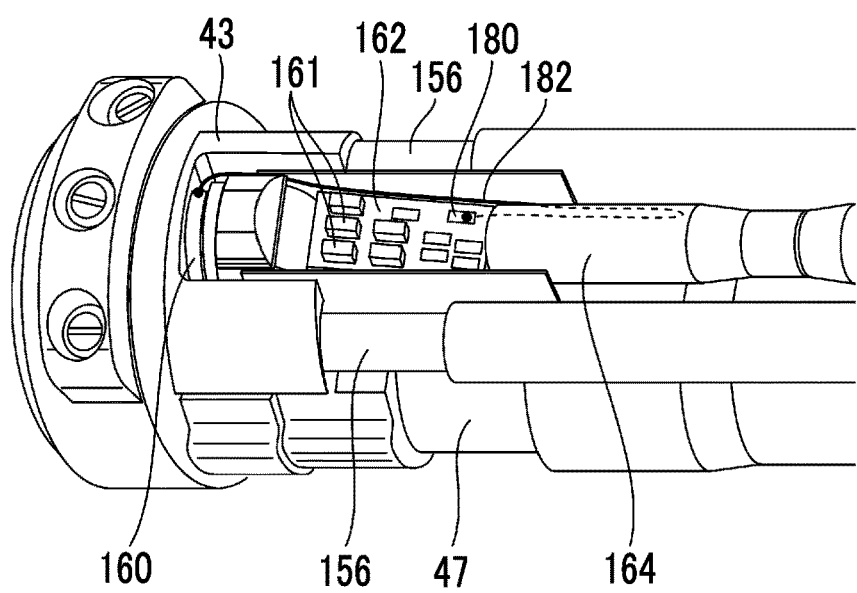
FIG. 5 is a perspective view showing the internal configuration of the distal end portion main body of the ultrasonic endoscope.

FIG. 1 is an overall view of the ultrasonic endoscope according to the embodiment of the present invention. FIG. 2 is a perspective view showing a distal end portion of an insertion portion of the ultrasonic endoscope. FIG. 3 is a side cross-sectional view of the distal end portion of the ultrasonic endoscope. FIG. 4 is a vertical cross-sectional view of a distal end portion main body of the endoscope. FIG. 5 is a perspective view showing the internal configuration of the distal end portion main body of the ultrasonic endoscope.

The ultrasonic endoscope 10 includes an operation portion 14 and an insertion portion 12 that is consecutively connected to the operation portion 14 and is inserted into a body. A universal cord 16 is connected to the operation portion 14. The universal cord 16 branches at an intermediate portion and one of branches thereof is attachably and detachably connected to an ultrasonic observation device 17 that generates an ultrasonic tomographic image. An ultrasonic diagnosis image generated by the ultrasonic observation device 17 is displayed on a monitor 50. In addition, a distal end of the other of the branches of the universal cord 16 is provided with an LG connector 18. The LG connector 18 is attachably and detachably connected to a light source device 20, so that illumination light is sent to illumination windows 52 provided at the distal end of the insertion portion 12. In addition, an electric connector 24 is connected to the LG connector 18 via a cable 22, and the electric connector 24 is attachably and detachably connected to a processor 26.

On the operation portion 14, an air/water supply button 28, a suction button 30, a shutter button 32, and a function switching button 34 are arranged to be parallel and the operation portion 14 is provided with a pair of angle knobs 36 and 36.

The insertion portion 12 is composed of a soft portion 40, a bendable portion 42, and a distal end portion 44 disposed in this order from the operation portion 14 side. The soft portion 40 is configured by covering an outer periphery of a spirally wound metal plate with a net to coat the outer periphery and has sufficient flexibility.

The bendable portion 42 is configured to be remotely curved in a case where the angle knobs 36 and 36 of the operation portion 14 are rotated. For example, regarding the bendable portion 42, a plurality of cylindrical angle rings are rotatably connected to each other by pins and a plurality of operation wires are inserted into the angle rings to be guided by the pins. In addition, in a case where the operation wires are pushed or pulled, the angle rings rotationally move, so that the bendable portion 42 is bent. It is possible to cause the distal end portion 44 to face a desired direction by bending the bendable portion 42.

As shown in FIG. 2, on an outer peripheral surface of a distal end portion main body 43 forming the distal end portion 44, an ultrasonic transducer 94 including an ultrasonic wave transmission/reception surface, in which a plurality of ultrasound oscillators 92 for acquisition of an ultrasonic tomographic image are arranged to be parallel, is disposed. The ultrasonic transducer 94 emits ultrasonic waves toward an observation target site and receives an echo signal thereof. In addition, in the case of an ultrasonic tomographic examination, a balloon (not shown) is mounted on the outer peripheral surface of the distal end portion 44 such that the balloon covers the ultrasonic transducer 94.

As shown in FIGS. 2 and 3, a distal end surface 45 of the distal end portion main body 43 includes the illumination windows 52 and an observation window 54. An illumination system 53 is provided behind the illumination windows 52, and an observation system 55 is provided behind the observation window 54. The illumination system 53 is composed of illumination lenses (not shown), fibers (not shown), and illumination metal bases 156 that hold the illumination lens and the fiber. Note that, in the present embodiment, the illumination metal bases 156 correspond to first metal members. The illumination lenses are disposed inside the illumination metal bases 156, and emission ends of the fibers are disposed behind the illumination lenses. The fiber is inserted into the insertion portion 12, the operation portion 14, and the universal cord 16 and an incidence end thereof is disposed in the LG connector 18.

The observation system 55 is composed of an observation lens (not shown), a lens barrel 160 holding the observation lens, and a substrate 162 on which an imaging element 161 is mounted. Note that, in the present embodiment, the lens barrel 160 corresponds to a second metal member. The observation window 54 is provided in the distal end surface 45 of the distal end portion 44, the imaging element 161 such as a complementary metal oxide semiconductor (CMOS) or a charge coupled device (CCD) is disposed behind the observation window 54 via the observation lens, and a signal cable 164 is connected to the substrate 162 that supports the imaging element 161. The signal cable 164 is inserted into the insertion portion 12, the operation portion 14, the universal cord 16, and the like and extends up to the electric connector 24 to be connected to the processor 26. Therefore, an observed image captured via the observation window 54 is formed on a light-receiving surface of the imaging element 161 and is converted into an electric signal. The electric signal is output to the processor 26 via the signal cable 164 and is converted into video signals. Accordingly, an observation image is displayed on the monitor 50 connected to the processor 26.

The distal end surface 45 of the distal end portion 44 is provided with a fluid jetting nozzle 56 and a treatment tool outlet port 58. The fluid jetting nozzle 56 provided at the distal end portion 44 communicates with a valve (not shown) operated by means of the air/water supply button 28. The valve communicates with an air/water supply connector 48 provided at the LG connector 18. An air/water supply unit (not shown) is connected to the air/water supply connector 48 for supply of air and water. Therefore, in a case where the air/water supply button 28 is operated, air or water is jetted toward the observation window 54 from the fluid jetting nozzle 56.

The treatment tool outlet port 58 provided at the distal end portion 44 communicates with a treatment tool insertion portion 46 via a treatment tool insertion channel 47. Therefore, it is possible to draw a treatment tool such as forceps out the treatment tool outlet port 58 by inserting the treatment tool through the treatment tool insertion portion 46. In addition, the treatment tool outlet port 58 communicates with a valve (not shown) operated by means of the suction button 30 and the valve is connected to a suction connector 49 of the LG connector 18. Therefore, it is possible to suck a lesion portion or the like through the treatment tool outlet port 58 by connecting a suction unit (not shown) to the suction connector 49 and operating the suction unit by means of the suction button 30.

Furthermore, the distal end portion 44 includes a communication path 90 that is open into an inner space of a balloon attached to the distal end portion 44. Through the communication path 90, a fluid is supplied or sucked with respect to the inner space of the balloon. Examples of the fluid include degassed water as an ultrasonic wave transmitting medium. Degassed water is supplied into the balloon to inflate the balloon and bring the balloon into contact with an observation target site in a body. Accordingly, air is removed from between the observation target site and the ultrasonic transducer, that is, from an ultrasonic wave scanning region, and thus attenuation of ultrasonic waves or echo signals is prevented. Note that in a case where the insertion portion 12 is to be pulled out from the inside of the body of a subject, the degassed water in the balloon is discharged from the communication path 90 so that the balloon contracts.

The communication path 90 communicates with a balloon air supply port 38 of the operation portion 14 shown in FIG. 1. A tube (not shown) is connected to the balloon air supply port 38, and a balloon control device (not shown) is connected to the balloon air supply port 38 via the tube. A fluid can be supplied to and sucked from the balloon with the balloon control device supplying or sucking the fluid.

(Configuration of Distal End Portion Main Body)

First Embodiment

Next, the configuration of the distal end portion main body 43 constituting the distal end portion 44 will be described. Since the ultrasound oscillators 92 of the ultrasonic endoscope 10 of the present embodiment are driven by a high voltage, the distal end portion main body 43 is formed of a resin material.

As shown in FIG. 4, the distal end portion main body 43 includes the illumination system 53, the observation system 55, first insertion holes 166 into which the illumination metal bases 156 of the illumination system 53 are inserted, and a second insertion hole 168 into which the lens barrel 160 of the observation system 55 is inserted. Further, the distal end portion main body 43 includes first fixing members 170 and first insert holes 172 into which the first fixing members 170 are inserted, the first fixing members 170 fixing the illumination metal bases 156 inserted into the first insertion holes 166 of the distal end portion main body 43 to the distal end portion main body 43 and having conductivity. In addition, the distal end portion main body 43 includes a second fixing member 174 and a second insert hole 176 into which the second fixing member 174 is inserted, the second fixing member 174 fixing the lens barrel 160 inserted into the second insertion hole 168 of the distal end portion main body 43 to the distal end portion main body 43 and having conductivity. The first insert holes 172 and the second insert hole 176 are formed along a direction orthogonal to a longitudinal axis of the insertion portion 12 and are provided to respectively penetrate into the first insertion holes 166 and the second insertion hole 168 from a side surface of the distal end portion main body 43. Accordingly, outer peripheral surfaces of the illumination metal bases 156 and an outer peripheral surface of the lens barrel 160 are pressed by the first fixing members 170 and the second fixing member 174 inserted through the side surface of the distal end portion main body 43, and thus the outer peripheral surfaces can be fixed to the distal end portion main body 43.

In addition, the distal end portion main body 43 includes an electrical connection member 178 that electrically connects the first fixing members 170 and the second fixing member 174 to each other. The electrical connection member 178 includes a contact surface 178a that comes into contact with the first fixing members 170 and a contact surface 178b that comes into contact with the second fixing member 174. As shown in FIG. 4, the electrical connection member 178 is provided along an outer periphery of the distal end portion main body 43, the contact surface 178a comes into contact with outer end portions of the first fixing members 170, and the contact surface 178b comes into contact with an outer end portion of the second fixing member 174, so that the illumination metal bases 156 and the lens barrel 160 are electrically connected to each other.

In addition, as shown in FIG. 5, the lens barrel 160 is connected to a ground terminal 180 provided on the substrate 162 via a jump wire 182. The ground terminal 180 is connected to the operation portion 14 via a jump wire (not shown). Since the illumination metal base 156 and the lens barrel 160 are electrically connected to each other by the electrical connection member 178 via the first fixing members 170 and the second fixing member 174, the illumination metal bases 156, the lens barrel 160, and the electrical connection member 178 can be connected to the ground. Note that although the lens barrel 160 and the ground terminal 180 are connected to each other via the jump wire 182 for connection to the ground in FIG. 5, the invention is not limited thereto. The connection to the ground may be performed by connecting the illumination metal bases 156 or the electrical connection member 178 to the ground terminal 180.

In a case where any of the lens barrel 160, the illumination metal bases 156, and the electrical connection member 178 is grounded, static electricity hitting the illumination system 53 or the observation system 55 can be released. According to the present embodiment, the lens barrel 160, the illumination metal bases 156, and the electrical connection member 178 are electrically connected to each other. Therefore, static electricity hitting the illumination system 53 or the observation system 55 can be released in a case where any of the lens barrel 160, the illumination metal bases 156, and the electrical connection member 178 is grounded.

Figure 6:
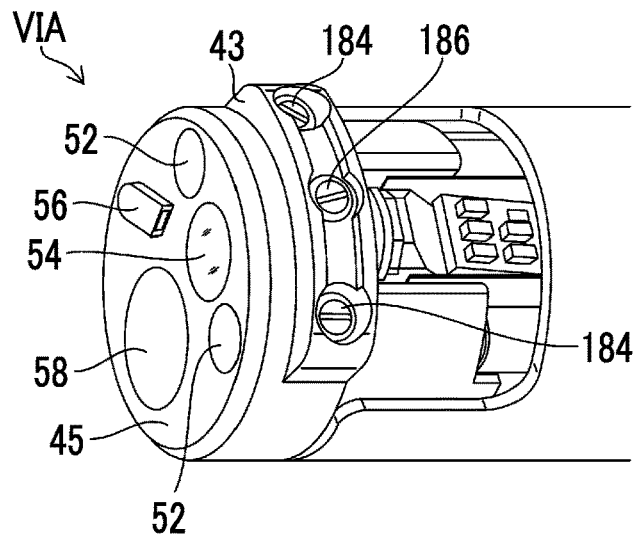
FIG. 6 is a view for describing a step of electrically connecting illumination metal bases and a lens barrel to each other.
Figure 6:
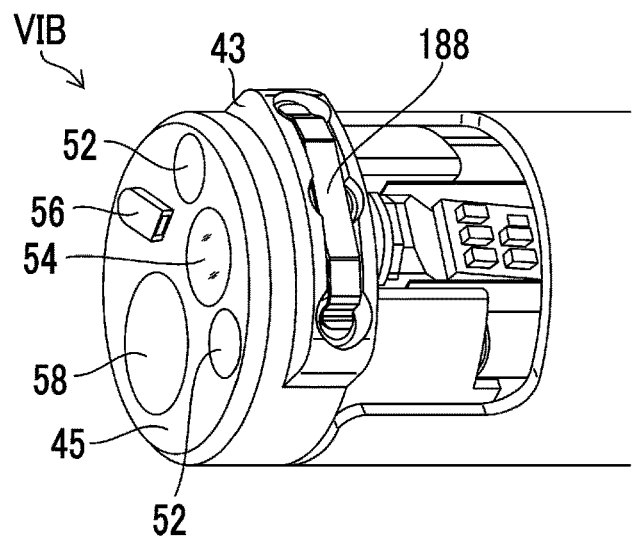
Figure 6:
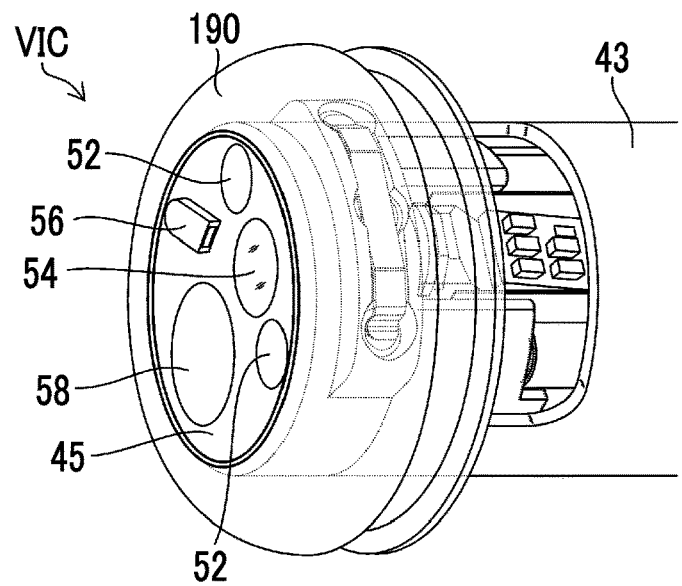

FIG. 6 is a view for describing a step of electrically connecting the illumination metal bases and the lens barrel to each other. In a first embodiment, the first fixing members 170 and the second fixing member 174 are screws and the electrical connection member 178 is a metal plate curved along an outer circumference of the distal end portion main body 43.

The distal end portion main body 43 of the ultrasonic endoscope 10 is provided with the illumination metal bases 156 of the illumination system 53 with the lens barrel 160 of the observation system 55 interposed therebetween (refer to FIG. 4). As shown in a perspective view VIA of FIG. 6, the illumination metal bases 156 (refer to FIG. 4) are fixed to the distal end portion main body 43 via screws 184 inserted into the first insert holes 172 (refer to FIG. 4). Similarly, the lens barrel 160 (refer to FIG. 4) is fixed to the distal end portion main body 43 via a screw 186 inserted into the second insert hole 176 (refer to FIG. 4).

Next, as shown in a perspective view VIB of FIG. 6, a metal plate 188 is disposed at a position where the first insert holes 172 into which the screws 184 are inserted and the second insert hole 176 into which the screw 186 is inserted are formed. The metal plate 188 includes contact surfaces (contact surfaces 178a and 178b in FIG. 4) that come into contact with the screws 184 and 186 respectively, and in a case where the contact surfaces come into contact with the screws 184 and 186, the illumination metal bases 156 and the lens barrel 160 are electrically connected to each other.

It is possible to fix the metal plate 188 to the distal end portion main body 43 by covering the distal end portion main body 43 with a cap 190 as shown in a perspective view VIC of FIG. 6 in a state where the metal plate 188 is disposed on a side surface of the distal end portion main body 43. The cap 190 includes a pressing surface (not shown) that presses and fixes the metal plate 188 to the distal end portion main body 43. Since the metal plate 188 is pressed and fixed by the cap 190, the metal plate 188 can be reliably brought into contact with the screws 184 and 186 and the metal plate 188 can be fixed to the distal end portion main body 43. The metal plate 188 may be a member curved along the outer circumference of the distal end portion main body 43 as shown in the perspective view VIB. In addition, a flat plate-shaped member may be disposed along an outer peripheral surface of the distal end portion main body 43 by being pressed by the cap 190.

According to the present embodiment, the illumination metal bases 156 and the lens barrel 160 are electrically connected to each other by the electrical connection member 178 and any of the illumination metal bases 156, the lens barrel 160, and the electrical connection member 178 is connected to the ground. Therefore, the number of connection wires such as jump wires for grounding can be one. In addition, the illumination system 53 and the observation system 55 can be fixed since the first fixing members 170 and the second fixing member 174 are inserted into the first insert holes 172 and the second insert hole 176 provided in the distal end portion main body 43 of the ultrasonic endoscope 10 and electrical connection can be established by means of a member that is disposed on the distal end portion main body 43 also in the related art since the first fixing members 170 and the second fixing member 174 are electrically connected to each other. Therefore, even in the case of a reduction in diameter, the amount of filling contents is not influenced and the imaging element can be prevented from being damaged by static electricity.

Second Embodiment

Figure 7:
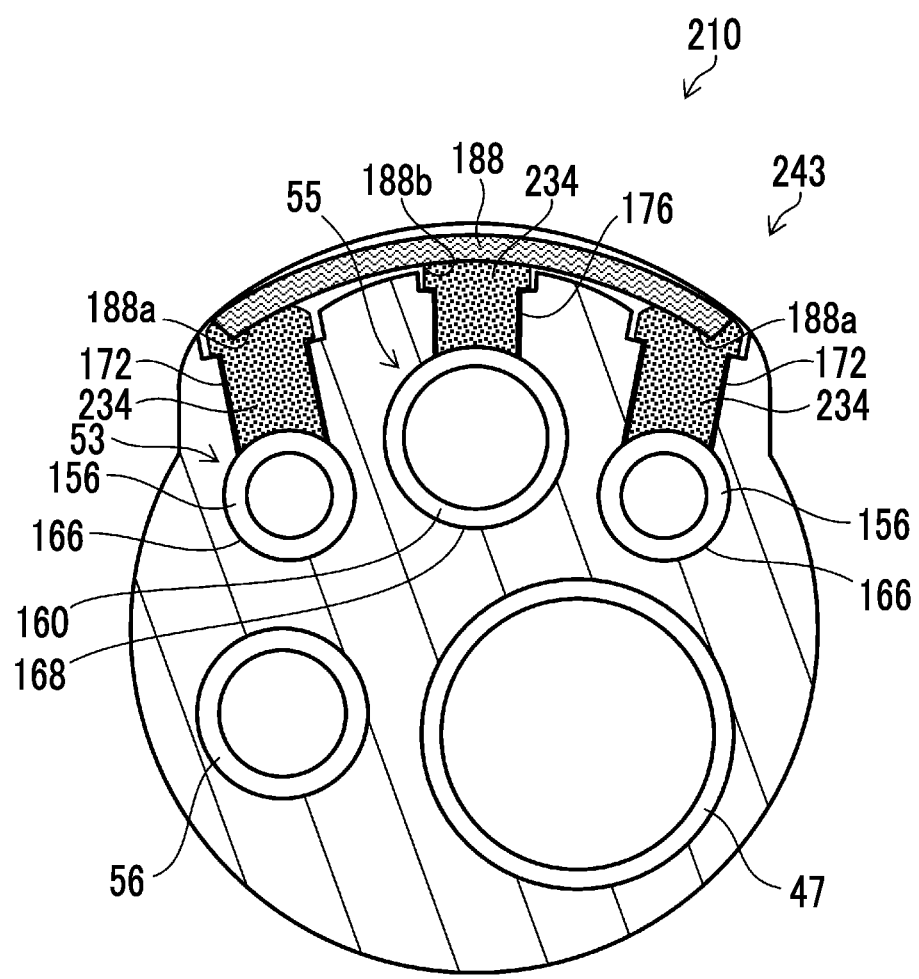
FIG. 7 is a vertical cross-sectional view of a distal end portion main body of a second embodiment.

FIG. 7 is a vertical cross-sectional view of a distal end portion main body 243 of an ultrasonic endoscope 210 of a second embodiment. The ultrasonic endoscope 210 of the second embodiment is different from the ultrasonic endoscope of the first embodiment in that conductive adhesives 234 are used as the first fixing members and the second fixing member.

In the ultrasonic endoscope 210 of the second embodiment, regarding the illumination metal bases 156 inserted into the first insertion holes 166, the illumination metal bases 156 and the distal end portion main body 243 are fixed to each other via the conductive adhesives 234 filling the first insert holes 172. Similarly, regarding the lens barrel 160 inserted into the second insertion hole 168, the lens barrel 160 and the distal end portion main body 243 are fixed to each other via the conductive adhesive 234 filling the second insert hole 176.

As an electrical connection member, the metal plate 188 is disposed on a side surface of the distal end portion main body 243 in which the first insert holes 172 and the second insert hole 176 are formed so that the conductive adhesives 234 filling the first insert holes 172 and the second insert hole 176 are electrically connected to each other. The metal plate 188 includes contact surfaces 188*a* and 188*b* that come into contact with the respective conductive adhesives 234 filling the first insert holes 172 and the second insert hole 176.

It is possible to press and fix the metal plate 188 to the distal end portion main body 243 by covering the distal end portion main body 243 with a cap as with the first embodiment in a state where the metal plate 188 is disposed on a side surface of the distal end portion main body 243. In addition, it is possible to reliably bring the metal plate 188 into contact with the conductive adhesives 234 by pressing and fixing the metal plate 188.

According to the ultrasonic endoscope 210 of the second embodiment, the conductive adhesives 234 are used as the first fixing members and the second fixing member. Therefore, even in a case where the spaces of the first insert holes 172 and the second insert hole 176 are small, it is possible to fix the illumination metal bases 156 and the lens barrel 160 to the distal end portion main body by filling the first insert holes 172 and the second insert hole 176 with the conductive adhesives 234. In addition, it is possible to electrically connect the illumination metal bases 156 and the lens barrel 160 to each other by bringing the conductive adhesives 234 into contact with the metal plate 188.

Third Embodiment

Figure 8:
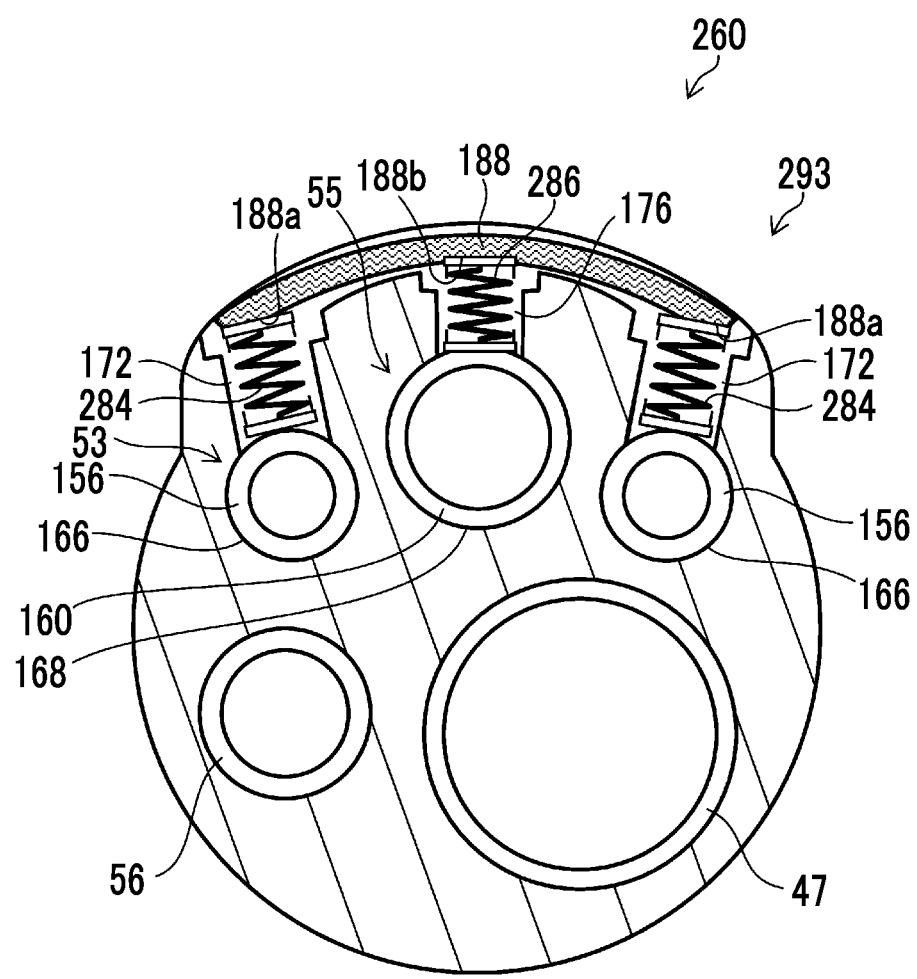
FIG. 8 is a vertical cross-sectional view of a distal end portion main body of a third embodiment.

FIG. 8 is a vertical cross-sectional view of a distal end portion main body 293 of an ultrasonic endoscope 260 of a third embodiment. The ultrasonic endoscope 260 of the third embodiment is different from the ultrasonic endoscopes of the other embodiments in that compression springs 284 and 286 are used as the first fixing members and the second fixing member.

In the ultrasonic endoscope 260 of the third embodiment, compression springs 284 and 286 are inserted into the first insert holes 172 and the second insert hole 176 as the first fixing members and the second fixing member. One end of each of the compression springs 284 inserted into the first insert holes 172 comes into contact with the illumination metal base 156 inserted into the first insertion hole 166. In addition, one end of the compression spring 286 inserted into the second insert hole 176 comes into contact with the lens barrel 160 inserted into the second insertion hole 168.

The other ends of the compression springs 284 and 286 come into contact with the metal plate 188 serving as the electrical connection member. The metal plate 188 includes the contact surfaces 188*a* and 188*b* that come into contact with the compression springs 284 and 286.

It is possible to press and fix the metal plate 188 by covering the distal end portion main body 293 with a cap as with the first embodiment in a state where the metal plate 188 is disposed on a side surface of the distal end portion main body 293. Since the metal plate 188 presses the compression springs 284 and 286 at the other ends of the compression springs 284 and 286, the illumination metal bases 156 and the lens barrel 160 can be fixed by the force of the pressed compression springs 284 and 286.

According to the third embodiment, the metal plate 188 presses the compression springs 284 and 286 for fixation and electrical connection between the illumination metal bases 156 and the lens barrel 160. Therefore, it is possible to reliably bring the compression springs 284 and 286 and the illumination metal bases 156 and the lens barrel 160 into contact with each other by using the restoring forces of the compression springs 284 and 286.

Fourth Embodiment

Figure 9:
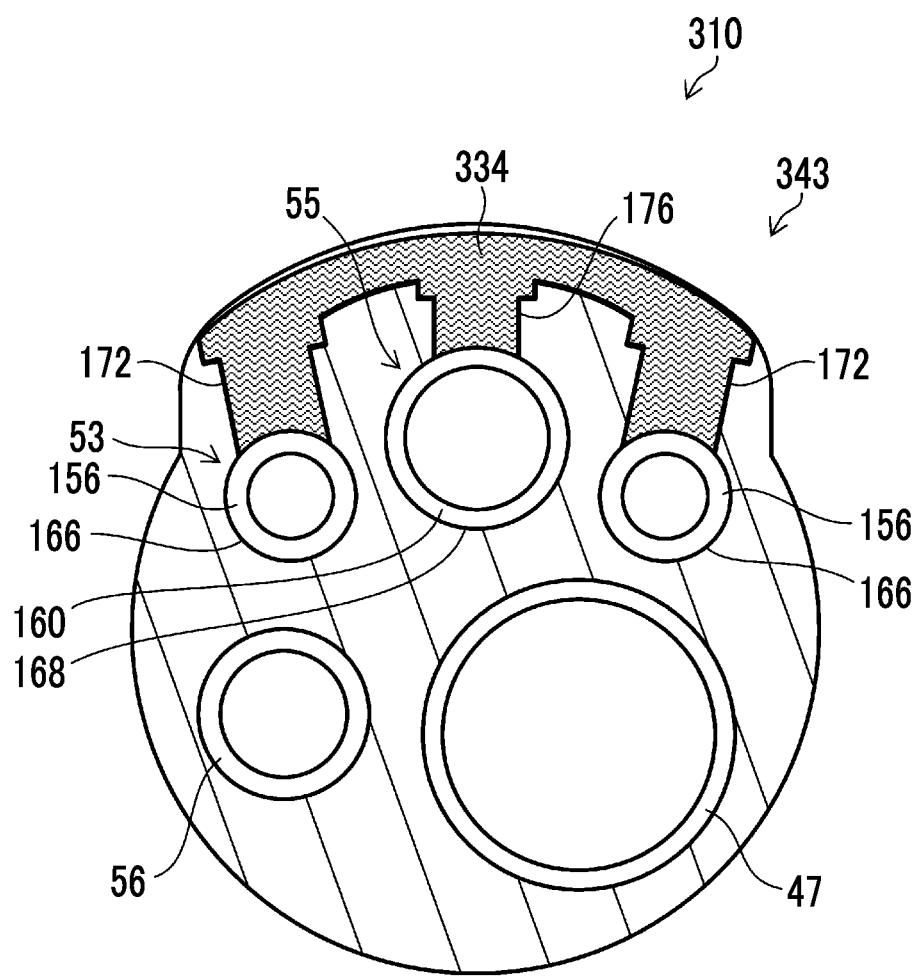
FIG. 9 is a vertical cross-sectional view of a distal end portion main body of a fourth embodiment.

FIG. 9 is a vertical cross-sectional view of a distal end portion main body 343 of an ultrasonic endoscope 310 of a fourth embodiment. The ultrasonic endoscope 310 of the fourth embodiment is different from the other embodiments in that the first fixing members, the second fixing member, and the electrical connection member are a conductive adhesive 334. Note that, although description about the conductive adhesive will be made below, there is no particular limitation as long as a material that has conductivity, exhibits fluidity when being applied, and solidifies in the atmosphere is used and silver paste or solder can be used as other materials, for example. As the silver paste, for example, a mixture of epoxy resin and silver can be used.

In the ultrasonic endoscope 310 of the fourth embodiment, regarding the illumination metal bases 156 inserted into the first insertion holes 166, the illumination metal bases 156 and the distal end portion main body 243 are fixed to each other via the conductive adhesive 334 filling the first insert holes 172. Similarly, regarding the lens barrel 160 inserted into the second insertion hole 168, the lens barrel 160 and the distal end portion main body 243 are fixed to each other via the conductive adhesive 234 filling the second insert hole 176.

In addition, in the ultrasonic endoscope 310 of the fourth embodiment, the conductive adhesive 334 is used as the electrical connection member, the conductive adhesive 334 filling the first insert holes 172 and the second insert hole 176 is applied along an outer circumference of the distal end portion main body 243, and the illumination metal bases 156 and the lens barrel 160 are electrically connected to each other by being connected to the conductive adhesive 334 filling the first insert holes 172 and the second insert hole 176. Accordingly, with the conductive adhesive 334, an integrally molded piece obtained by integrally molding the first fixing members, the second fixing member, and the electrical connection member can be achieved.

According to the fourth embodiment, the first fixing members, the second fixing member, and the electrical connection member are integrally formed with each other by means of the conductive adhesive 334. Therefore, the illumination metal bases 156 and the lens barrel 160 can be reliably electrically connected to each other. In addition, since the conductive adhesive 334 is used as the first fixing members and the second fixing member, even in a case where the diameters of the first insert holes 172 and the second insert hole 176 are small, fixation to the distal end portion main body 343 can be made with the conductive adhesive 334 filling the first insert holes 172 and the second insert hole 176.

Fifth Embodiment

Figure 10:
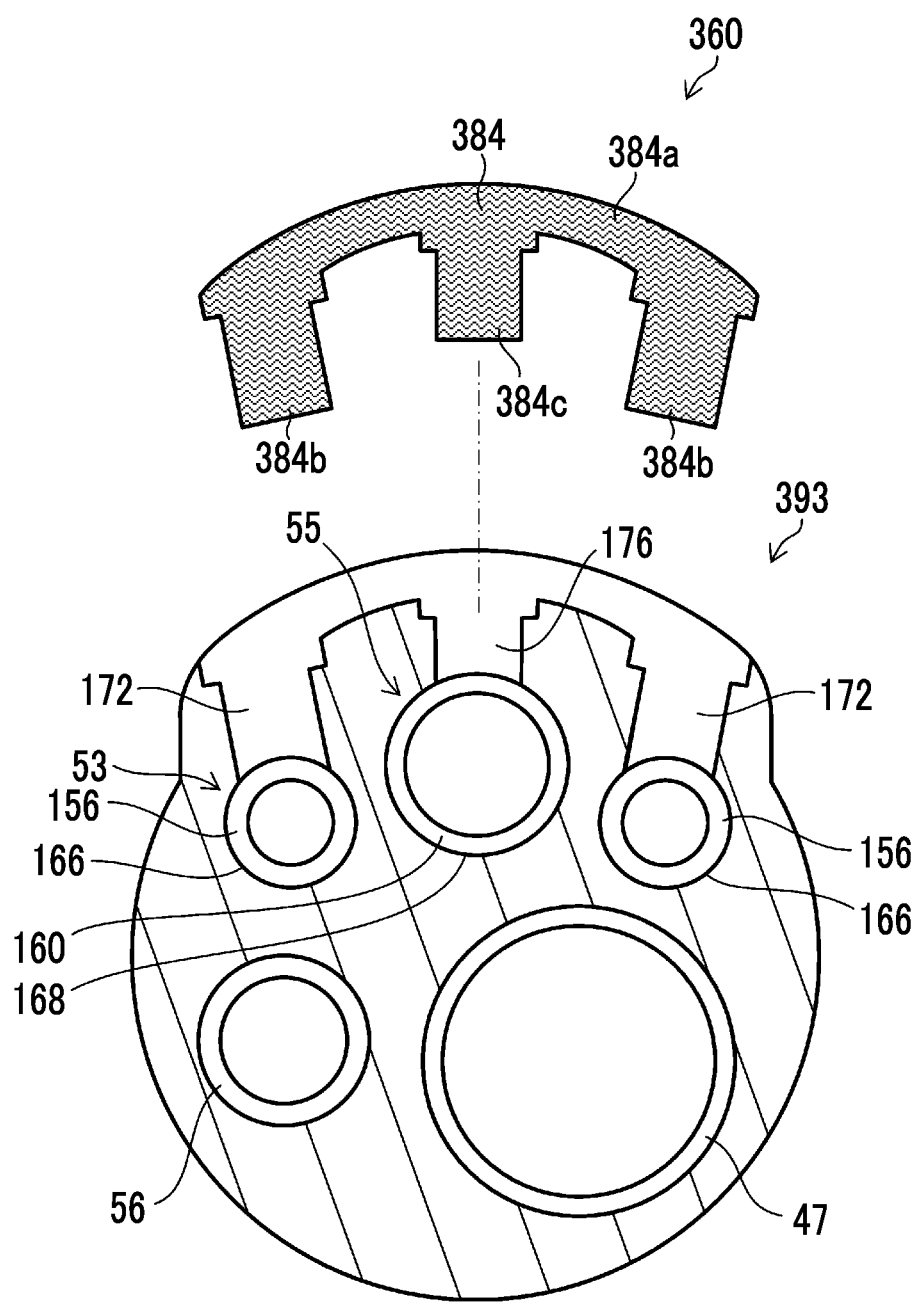
FIG. 10 is a vertical cross-sectional view of a distal end portion main body of a fifth embodiment.

FIG. 10 is a vertical cross-sectional view of a distal end portion main body 393 of an ultrasonic endoscope 360 of a fifth embodiment. The ultrasonic endoscope 360 of the fifth embodiment is different from the other embodiments in that a first fixation portion, a second fixation portion, and the electrical connection member are a conductive rubber and an integrally molded piece obtained by integrally forming the first fixation portion, the second fixation portion, and the electrical connection member with each other.

In the ultrasonic endoscope 360 of the fifth embodiment, a conductive rubber 384 is used as the first fixation portion, the second fixation portion, and the electrical connection member, and a support portion 384a disposed along the outer circumference of the distal end portion main body 393 includes first protrusion portions 384b to be inserted into the first insert holes 172 and a second protrusion portion 384c to be inserted into the second insert hole 176. The heights of the first protrusion portions 384b and the second protrusion portion 384c are larger than the depths of the first insert holes 172 and the second insert hole 176, respectively. Accordingly, in a case where the conductive rubber 384 is pressed and fixed by means of a cap after the integrally molded conductive rubber 384 is disposed on the distal end portion main body 393, the first protrusion portions 384b and the illumination metal bases 156 come into contact with each other and thus fixation to the distal end portion main body 393 can be achieved. Similarly, the second protrusion portion 384c and the lens barrel 160 come into contact with each other and thus the lens barrel 160 can be fixed to the distal end portion main body 393.

According to the fifth embodiment, since the first fixing members, the second fixing member, and the electrical connection member are integrally molded with each other, the illumination metal bases 156 and the lens barrel 160 can be reliably electrically connected to each other. In addition, since the conductive rubber 384 is used, the illumination metal bases 156 and the lens barrel 160 can be reliably fixed by means of expansion and contraction of the rubber.

Sixth Embodiment

Figure 11:
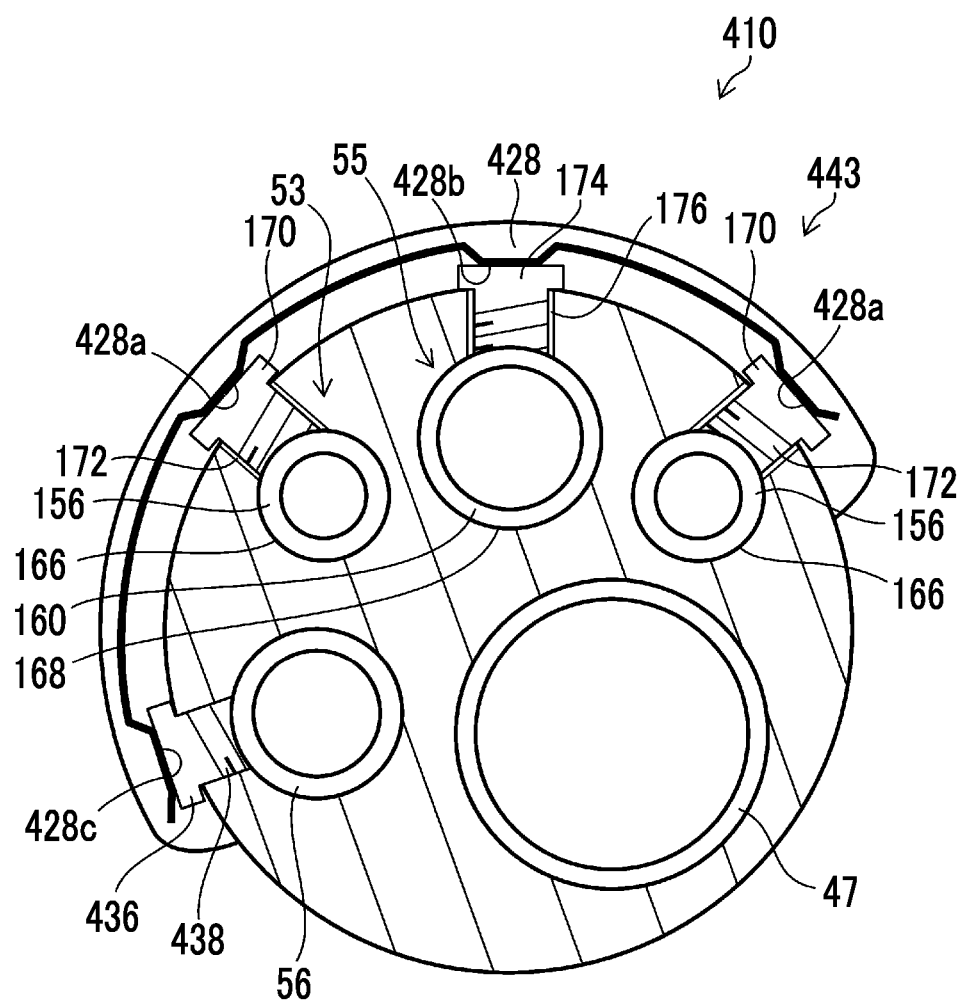
FIG. 11 is a vertical cross-sectional view of a distal end portion main body of a sixth embodiment.

FIG. 11 is a vertical cross-sectional view of a distal end portion main body 443 of an ultrasonic endoscope 410 of a sixth embodiment. In the ultrasonic endoscope 410 of the sixth embodiment, an electrical connection member 428 includes contact surfaces 428a that come into contact with the first fixing members 170, a contact surface 428b that comes into contact with the second fixing member 174, and a contact surface 428c that comes into contact with a third fixing member 436 fixing the fluid jetting nozzle 56 to the distal end portion main body 443.

The distal end surface 45 of the distal end portion 44 of the ultrasonic endoscope 410 is provided with the fluid jetting nozzle 56 and a proximal end side of the fluid jetting nozzle 56 communicates with the operation portion 14. The distal end portion main body 443 of the ultrasonic endoscope 410 includes the third fixing member 436 that fixes the fluid jetting nozzle 56 to the distal end portion main body 443 and a third insert hole 438 into which the third fixing member 436 is inserted. Since the electrical connection member 428 includes the contact surfaces 428a, 428b, and 428c, the electrical connection member 428 comes into contact with the first fixing members 170, the second fixing member 174, and the third fixing member 436 and can electrically connect the illumination metal bases 156, the lens barrel 160, and the fluid jetting nozzle 56 to each other. In addition, by connecting any of the illumination metal bases 156, the lens barrel 160, the fluid jetting nozzle 56, and the electrical connection member 428 to the ground, it is possible to prevent static electricity hitting the fluid jetting nozzle 56 from running through a space between the fluid jetting nozzle 56 and the imaging element 161 and hitting the imaging element 161.

Note that the electrical connection member 428 may be the same as that of the first to fifth embodiments. In addition, the third fixing member 436 may be the same as that of the first to fifth embodiments. In addition, in FIG. 11, an example in which the electrical connection member 428 is one member that comes into contact with the first fixing members 170, the second fixing member 174, and the third fixing member 436 has been described. However, the electrical connection member 428 may be a plurality of members as long as the members can be electrically connected to each other. For example, an electrical connection member that comes into contact with the first fixing members 170 and the second fixing member 174 may be brought into contact with an electrical connection member that comes into contact with the third fixing member 436 so that the illumination metal bases 156, the lens barrel 160, and the fluid jetting nozzle 56 are electrically connected to each other.

Seventh Embodiment

Figure 12:
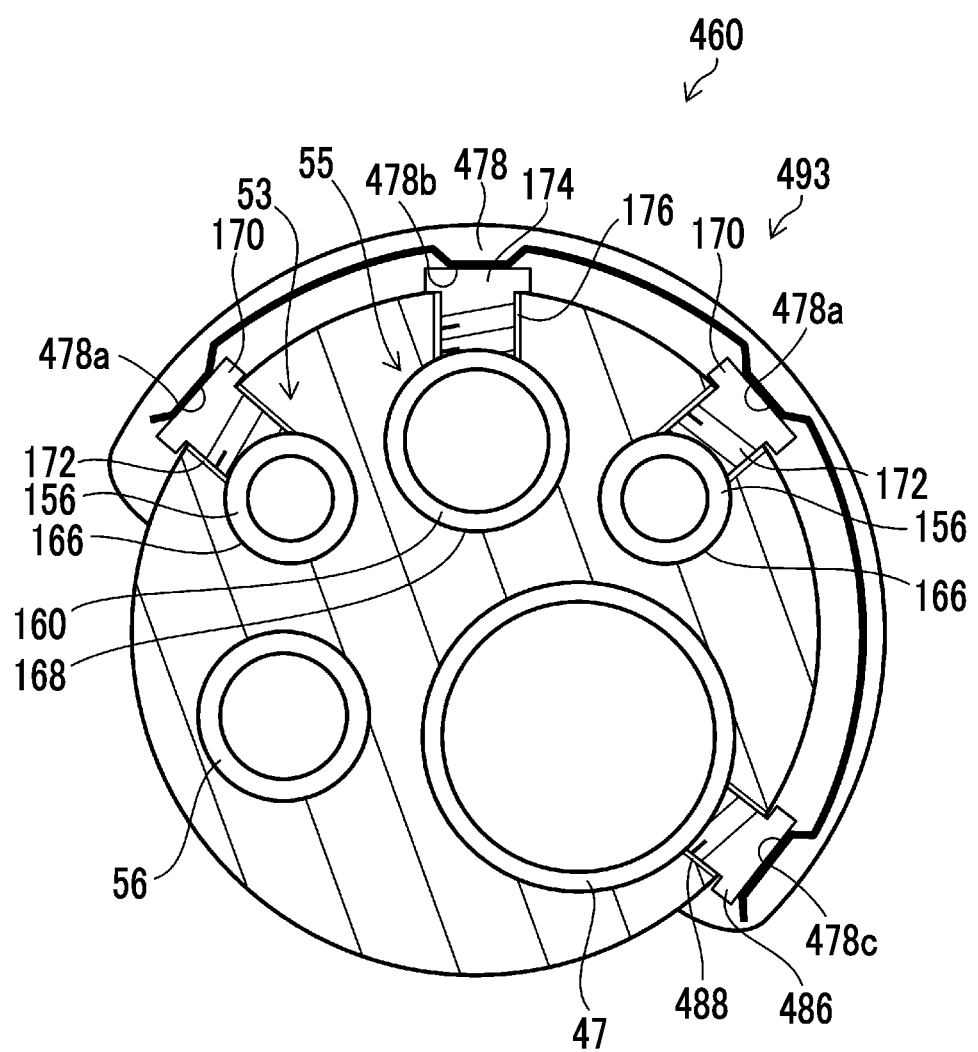
FIG. 12 is a vertical cross-sectional view of a distal end portion main body of a seventh embodiment.

FIG. 12 is a vertical cross-sectional view of a distal end portion main body 493 of an ultrasonic endoscope 460 of a seventh embodiment. In the ultrasonic endoscope 460 of the seventh embodiment, an electrical connection member 478 includes contact surfaces 478a that come into contact with the first fixing members 170, a contact surface 478b that comes into contact with the second fixing member 174, and a contact surface 478c that comes into contact with a fourth fixing member 486 fixing the treatment tool insertion channel 47 to the distal end portion main body 493.

The distal end surface 45 of the distal end portion 44 of the ultrasonic endoscope 460 is provided with the treatment tool outlet port 58 and a proximal end side of the treatment tool outlet port 58 communicates with the treatment tool insertion portion 46 via the treatment tool insertion channel 47. The distal end portion main body 493 of the ultrasonic endoscope 460 includes the fourth fixing member 486 that fixes the treatment tool insertion channel 47 to the distal end portion main body 493 and a fourth insert hole 488 into which the fourth fixing member 486 is inserted. Since the electrical connection member 478 includes the contact surfaces 478*a*, 478*b*, and 478*c*, the electrical connection member 478 comes into contact with the first fixing members 170, the second fixing member 174, and the fourth fixing member 486 and can electrically connect the illumination metal bases 156, the lens barrel 160, and the treatment tool insertion channel 47 to each other. In addition, by connecting any of the illumination metal bases 156, the lens barrel 160, the treatment tool insertion channel 47, and the electrical connection member 478 to the ground, it is possible to prevent static electricity hitting the treatment tool insertion channel 47 from running through a space between the treatment tool insertion channel 47 and the imaging element 161 and hitting the imaging element 161.

Note that the electrical connection member 478 may have the same configuration as that of the first to fifth embodiments. In addition, the fourth fixing member 486 may be the same as that of the first to fifth embodiments. In addition, in FIG. 12, an example in which the electrical connection member 478 is one member that comes into contact with the first fixing members 170, the second fixing member 174, and the fourth fixing member 486 has been described. However, the electrical connection member 478 may be a plurality of members as long as the members can be electrically connected to each other. For example, an electrical connection member that comes into contact with the first fixing members 170 and the second fixing member 174 may be brought into contact with an electrical connection member that comes into contact with the fourth fixing member 486 so that the illumination metal bases 156, the lens barrel 160, and the treatment tool insertion channel 47 are electrically connected to each other.

In addition, although a configuration in which the illumination metal bases 156, the lens barrel 160, and the fluid jetting nozzle 56 or the treatment tool insertion channel 47 are electrically connected to each other has been described in the sixth embodiment and the seventh embodiment, all of the illumination metal bases 156, the lens barrel 160, the fluid jetting nozzle 56, and the treatment tool insertion channel 47 may be electrically connected to each other.

Eighth Embodiment

Figure 13:
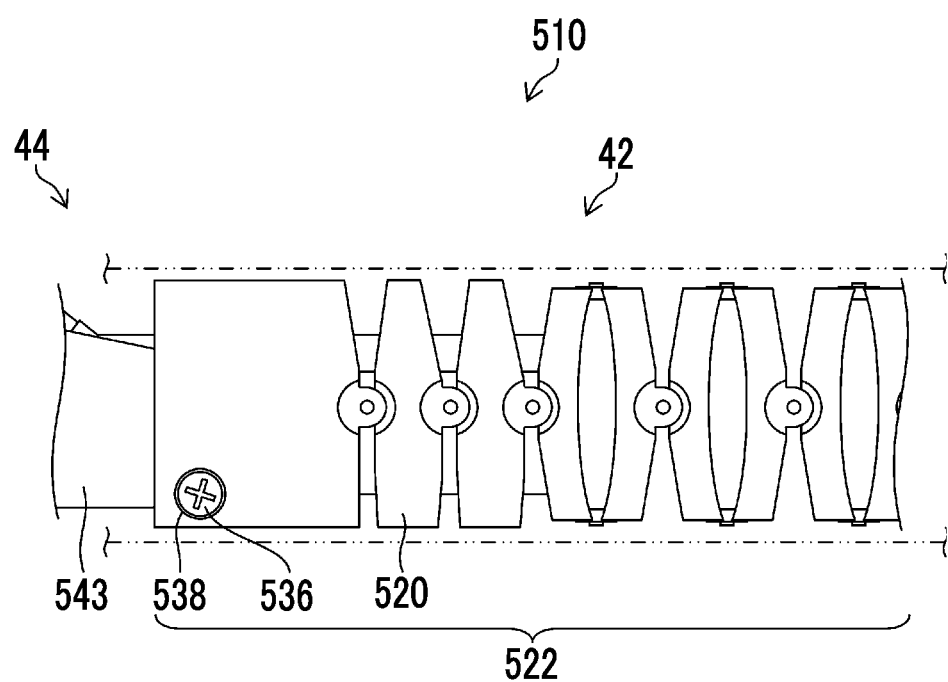
FIG. 13 is a view of a connection portion between a distal end portion and a bendable portion of an ultrasonic endoscope.

FIG. 13 is a view of a connection portion between the distal end portion 44 and the bendable portion 42 of an ultrasonic endoscope 510. In the case of the ultrasonic endoscope 510 of an eighth embodiment, the lens barrel 160 is grounded by means of connection to a fifth fixing member 536 that fixes a metal ring group 522 to a distal end portion main body 543, the metal ring group 522 consisting of a plurality of angle rings 520 connected to a proximal end side of the distal end portion main body 543. The lens barrel and the fifth fixing member 536 can be connected to each other via a jump wire (not shown). Like the distal end portion main body of the ultrasonic endoscope in the above-described first to seventh embodiments, the distal end portion main body 543 is electrically connected to the illumination metal bases 156 and the lens barrel 160. In addition, the distal end portion main body 543 may be electrically connected to the fluid jetting nozzle 56 or the treatment tool insertion channel 47.

The insertion portion 12 includes the fifth fixing member 536 that fixes the metal ring group 522 and the distal end portion main body 543 at a distal end side of the metal ring group 522 and a fifth insert hole 538 into which the fifth fixing member 536 is inserted. The metal ring group 522 is connected to the operation portion 14 via a jump wire (not shown) and thus the lens barrel 160 can be connected to the ground. Since the lens barrel 160 and the fifth fixing member 536 are connected to each other, static electricity hitting the illumination metal bases 156, the lens barrel 160, and the fluid jetting nozzle 56 or the treatment tool insertion channel 47 can be released to the ground via the metal ring group 522 provided at the bendable portion 42.

EXPLANATION OF REFERENCES

10, 210, 260, 310, 360, 410, 460, 510: Ultrasonic endoscope
12: Insertion portion
14: Operation portion
16: Universal cord
17: Ultrasonic observation device
18: LG connector
20: Light source device
22: Cable
24: Electric connector
26: Processor
28: Air/water supply button
30: Suction button
32: Shutter button
34: Function switching button
36: Angle knob
38: Balloon air supply port
40: Soft portion
42: Bendable portion
43, 243, 293, 343, 393, 443, 493, 543: Distal end portion main body
44: Distal end portion
45: Distal end surface
46: Treatment tool insertion portion
47: Treatment tool insertion channel
48: Air/water supply connector
49: Suction connector
50: Monitor
52: Illumination window
53: Illumination system
54: Observation window
55: Observation system
56: fluid jetting nozzle
58: Treatment tool outlet port
90: Communication path
92: Ultrasound oscillator
94: Ultrasonic transducer
156: Illumination metal base
160: lens barrel
161: Imaging element
162: Substrate
164: Signal cable
166: First insertion hole
168: Second insertion hole
170: First fixing member
172: First insert hole
174: Second fixing member
176: Second insert hole
178, 428, 478: Electrical connection member
178*a*, 178*b*, 428*a*, 428*b*, 428*c*, 478*a*, 478*b*, 478*c*: Contact surface
180: Ground terminal
182: Jump wire
184, 186: Screw
188: Metal plate 188a, 188b: Contact surface
190: Cap
234, 334: Conductive adhesive
284: Compression spring
286: Compression spring
293: Distal end portion main body
384: Conductive rubber
384a: Support portion
384b: First protrusion portion
384c: Second protrusion portion
436: Third fixing member
438: Third insert hole
486: Fourth fixing member
488: Fourth insert hole
520: Angle ring
522: Metal ring group
536: Fifth fixing member
538: Fifth insert hole

What is claimed is:

1. An ultrasonic endoscope comprising:
a distal end portion including a distal end portion main body that is provided at a distal end side of an insertion portion and is formed of a resin material and an ultrasound oscillator that is provided at the distal end portion main body,
wherein the distal end portion main body includes
an illumination system that includes an illumination lens, a fiber, and a first metal member holding the illumination lens and the fiber,
a first insertion hole into which the first metal member is inserted,
a first fixing member that fixes the first metal member inserted into the first insertion hole to the distal end portion main body and that has conductivity,
a first insert hole into which the first fixing member is inserted,
an observation system that includes an observation lens, a second metal member holding the observation lens, and a substrate on which an imaging element is mounted,
a second insertion hole into which the second metal member is inserted,
a second fixing member that fixes the second metal member inserted into the second insertion hole to the distal end portion main body and that has conductivity,
a second insert hole into which the second fixing member is inserted, and
an electrical connection member that electrically connects the first fixing member and the second fixing member to each other, and
at least one of the first metal member, the second metal member, or the electrical connection member is connected to a ground.

2. The ultrasonic endoscope according to claim 1,
wherein the first insert hole and the second insert hole are formed along a direction orthogonal to a longitudinal axis of the insertion portion, and
the first insert hole penetrates into the first insertion hole from a side surface of the distal end portion main body and the second insert hole penetrates into the second insertion hole from the side surface of the distal end portion main body.

3. The ultrasonic endoscope according to claim 2,
wherein the first fixing member and the second fixing member are screws, and
the electrical connection member is a metal plate that is disposed on an outer circumference of the distal end portion main body and that includes a contact surface coming into contact with the screws.

4. The ultrasonic endoscope according to claim 2,
wherein the first fixing member and the second fixing member are conductive adhesives, and
the electrical connection member is a metal plate that is disposed on an outer circumference of the distal end portion main body and that includes a contact surface coming into contact with the conductive adhesives.

5. The ultrasonic endoscope according to claim 2,
wherein the first fixing member and the second fixing member are compression springs, and
the electrical connection member is a metal plate that is disposed on an outer circumference of the distal end portion main body and that includes a contact surface coming into contact with the compression springs.

6. The ultrasonic endoscope according to claim 2,
wherein the first fixing member, the second fixing member, and the electrical connection member are conductive adhesives, silver paste, or solder, and
the first fixing member, the second fixing member, and the electrical connection member are an integrally molded piece obtained by connecting the conductive adhesives, the silver paste, or the solder filling the first insert hole and the second insert hole by the conductive adhesives, the silver paste, or the solder disposed along an outer circumference of the distal end portion main body.

7. The ultrasonic endoscope according to claim 2,
wherein the first fixing member, the second fixing member, and the electrical connection member are conductive rubbers, and
the first fixing member, the second fixing member, and the electrical connection member are an integrally molded piece.

8. The ultrasonic endoscope according to claim 1, further comprising:
a cap that includes a pressing surface pressing and fixing the electrical connection member to the distal end portion main body.

9. The ultrasonic endoscope according to claim 1,
wherein the distal end portion main body includes a fluid jetting nozzle, a third fixing member that fixes the fluid jetting nozzle to the distal end portion main body and that has conductivity, and a third insert hole into which the third fixing member is inserted, and
the electrical connection member includes a contact surface that comes into contact with the third fixing member.

10. The ultrasonic endoscope according to claim 1,
wherein the distal end portion main body includes a treatment tool insertion channel, a fourth fixing member that fixes the treatment tool insertion channel to the distal end portion main body and that has conductivity, and a fourth insert hole into which the fourth fixing member is inserted, and
the electrical connection member includes a contact surface that comes into contact with the fourth fixing member.

11. The ultrasonic endoscope according to claim 1,
wherein the connection to the ground is connection between a ground terminal provided on the substrate and the second metal member.

12. The ultrasonic endoscope according to claim 1,
wherein the insertion portion includes a metal ring group consisting of a plurality of angle rings connected to a proximal end side of the distal end portion main body,
a fifth fixing member that fixes the metal ring group to the distal end portion main body and that has conductivity and a fifth insert hole into which the fifth fixing member is inserted are provided, and
the connection to the ground is connection between the fifth fixing member and the second metal member.

* * * * *